United States Patent
Colonna

Patent Number: 5,149,323
Date of Patent: Sep. 22, 1992

[54] SELF DESTRUCT DOUBLE SYRINGE

[76] Inventor: John P. Colonna, 1183 Coquille St., Sarasota, Fla. 34242

[21] Appl. No.: 681,991

[22] Filed: Apr. 8, 1991

[51] Int. Cl.$^5$ .................................................. A61M 5/00
[52] U.S. Cl. ..................................... 604/110; 604/218
[58] Field of Search ................ 604/110, 187, 218, 228

[56] References Cited

U.S. PATENT DOCUMENTS

| | | | |
|---|---|---|---|
| 4,699,614 | 10/1987 | Glazier | 604/110 |
| 4,775,363 | 10/1988 | Sandsdalen | 604/110 |
| 4,863,427 | 9/1989 | Cocchi | 604/110 |
| 4,908,020 | 3/1990 | Pettersen | 604/110 |

FOREIGN PATENT DOCUMENTS

| | | | |
|---|---|---|---|
| 2646086 | 10/1990 | France | 604/110 |
| 2646087 | 10/1990 | France | 604/110 |
| 89/09074 | 10/1989 | World Int. Prop. O. | 604/110 |

Primary Examiner—John D. Yasko
Attorney, Agent, or Firm—Dykema Gossett

[57] ABSTRACT

The present invention relates to a self destructing syringe which is only capable of being used once and is thereafter rendered useless. The syringe has a plunger and plunger rod which are interconnected by a coupling assembly. This coupling assembly includes a receiver which is hollow and extends outwardly from the plunger and a connector which is in the form of an enlarged head on the end of the plunger rod which is adapted to be inserted into the receiver. In the preferred embodiment, the receiver has longitudinal splits along the side wall which form outwardly biased fingers. The coupling assembly also includes a locking sleeve which is adapted to slide over the receiver to prevent the connector from being released from the receiver when the locking sleeve is in place. The locking sleeve remains in place as the plunger rod is pulled away from the needle to draw fluid into the syringe and moves away from the receiver as the plunger rod is pushed toward the needle to discharge the fluid from the syringe. The locking sleeve frictionally engages the inner wall of the housing and is wedged against the housing when the plunger rod is pushed towards the needle. Simultaneously, the fingers spring outwardly against the inner wall of the housing. Thereafter, there is nothing to hold the plunger rod is the receiver and if the needle is attempted to be used again, the plunger rod is released from the syringe rendering the syringe useless.

18 Claims, 1 Drawing Sheet

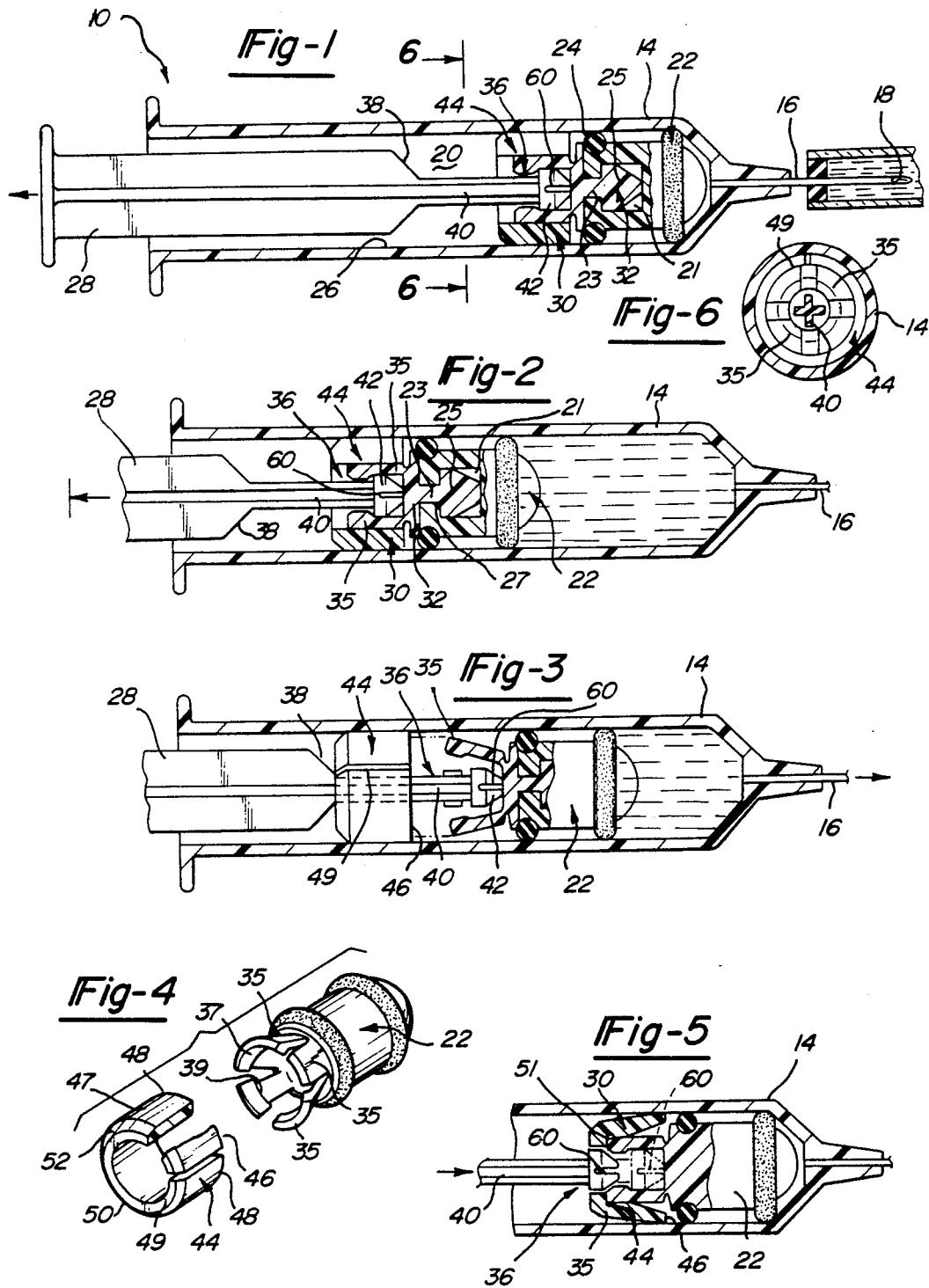

SELF DESTRUCT DOUBLE SYRINGE

BACKGROUND OF THE INVENTION

The present invention relates to a syringe and more particularly to a self destructing syringe which can only be used once and is thereafter rendered useless.

Among many of the problems facing the world today, drugs and AIDS are two of the most devastating problems and the two are very much intertwined. It is the belief of researchers that a large contributing factor to the spread of AIDS is intravenous drug use. It is believed that drug users commonly share syringes used to inject drugs which in turn spreads the AIDS virus between users of the same needle. Further spreading of the AIDS virus is through further contact with the AIDS carrier either through further sharing of needles or other contact.

In an effort to reduce the occurrence of needle or syringe sharing by drug users and thereby to try and reduce the spread of the AIDS virus, the United States government is planning to freely distribute syringes to intravenous drug users. It is the thought that by giving away syringes and making them freely accessible, there will be less likelihood that users will share needles and ultimately it is hoped that the spread of AIDS virus will be reduced.

Although this plan may in fact reduce the spread of AIDS, there is no assurance that intravenous drug users will not stop sharing needles even if they receive them for free. It is not beyond reason that there will continue to be sharing of syringes even after the government begins to freely supply them. In view of this continued possibility for the sharing of syringes and the resultant spread of the AIDS virus, there has been great interest in the medical community for the development of a syringe which can only be used once and is thereafter rendered useless.

BRIEF DESCRIPTION OF THE INVENTION

The present invention provides a solution to the problem of syringes being used more than once and is an economical way to solve the problem. The present invention provides a self destructing syringe that can only be used once while functioning in the same manner as an ordinary syringe during the initial use of the syringe. After the initial use, the plunger rod and plunger are automatically disconnected preventing any further use of the syringe.

As with conventional syringes, the syringe of the present invention includes a needle having a passage which is affixed to a hollow outer housing which has an interior cavity. The passage is in communication with the interior cavity of the housing so that fluid can be drawn into the cavity of the housing. A plunger and plunger rod are operatively received within the cavity and are adapted to reciprocate within the cavity to draw fluid into the housing.

The plunger rod of the present invention is selectively coupled to the plunger to control movement of the plunger within the cavity. A coupling means is provided to selectively couple the plunger and the plunger rod so that the plunger and rod are initially coupled to permit the plunger to be drawn away from the needle to draw fluid into the cavity and to be pushed toward the needle to issue fluid from the cavity and needle. The coupling means automatically disconnects the plunger and plunger rod after the plunger is pushed forward so that the plunger can only be pushed forward toward the needle and cannot thereafter be drawn away from the needle a second time. If the plunger rod is pulled a second time, it is disconnected from the plunger.

The coupling means includes separable mating members, one extends from the plunger and the other extends from the plunger rod. A locking member is adapted to selectively interlock these mating members so that the plunger rod and plunger are interconnected. The separable mating members include a connector and a receiver which is adapted to accept the connector. In the preferred embodiment, the receiver is a tube with the walls of the tube being split longitudinally to form fingers that are normally biased outwardly against the inside wall of the syringe housing. The connector of the preferred embodiment is a shaft which ends in an enlarged head member. This head member is captured by the fingers of the receiver and the fingers are locked about the head portion by a locking means.

The locking means of the preferred embodiment includes a tubular sleeve which is reciprocally mounted upon the plunger rod adjacent the connector. The sleeve is adapted to slide over the receiver means upon initial coupling of the receiver and the connector to interlock the receiver and connector. The tubular sleeve of the locking means slides over the receiver to bias and lock the fingers of the receiver about the connector.

When the syringe is used, the locking sleeve is initially over the receiver so that the plunger rod and plunger can be pulled away from the needle as a unit to draw fluid into the cavity of the outer housing. As the plunger rod is pushed in the direction of the needle, the locking sleeve slides away from the receiver due to frictional engagement between the sleeve and the inner walls of the housing. As the plunger rod continues to be forced towards the needle, the sleeve completely frees itself from the receiver and engages the inner walls of the outer housing in a manner such that it is not capable of sliding within the cavity. Simultaneously, the fingers of the receiver spring open and engage the inner walls of the housing preventing the locking sleeve from being slid over the receiver. After the plunger reaches the end of its travel, any attempt to move the plunger away from the needle a second time will result in the plunger rod disengaging from the plunger with the plunger remaining fixed in the housing rendering the syringe useless for further injections.

BRIEF DESCRIPTION OF THE DRAWINGS

FIG. 1 is a cross-sectional view of the self destructing syringe of the present invention prior to its initial use.

FIG. 2 is a cross-sectional view of the self destructing syringe of the present invention illustrating the drawing of the plunger by the plunger rod to draw fluid into the syringe.

FIG. 3 is a cross-sectional view of the syringe of the present invention illustrating the use of the syringe to inject fluid from the syringe and the release of the coupling between the plunger rod and plunger.

FIG. 4 is an exploded view of the receiver attached to the plunger and the locking sleeve.

FIG. 5 is a partial cross-sectinal view of the assembly process of the syringe of the present invention.

FIG. 6 is a cross-sectional view taken along line 6—6 in FIG. 1.

DETAILED DESCRIPTION OF THE INVENTION

With reference to FIG. 1, the syringe of the present invention is shown generally at 10. The syringe includes a casing or outer housing 14 which defines an interior chamber 20. As with conventional syringes, this interior chamber is designed to receive fluid or medicant as a vacuum is created in the chamber by drawing plunger 22 away from needle 16. Needle 16 is mounted at the forward end of the housing 14. Needle 16 has a hollow passage 18 which is in communication with the interior chamber 20 so that fluid can be drawn through the needle into the chamber.

Plunger 22 is reciprocally mounted in housing 14 and is of conventional design having ribs 24 extending outwardly from the body of the plunger which engage the interior walls 26 of housing 14. The ribs 24 engage the wall 26 to create a seal such that a vacuum can be drawn in chamber 20 between the plunger and the needle. As should be appreciated, other types of plungers can be used without detracting from the present invention. A plunger rod 28 is selectively coupled to plunger 22 so that plunger 22 can be pulled rearwardly away from needle 16 and pushed forwardly toward needle 16 one time. Thereafter, rod 28 is automatically released from plunger 22 so that the plunger cannot be moved a second time.

With reference to FIG. 2, the coupling means 30 which couples plunger rod 28 to plunger 22 is illustrated. The coupling means is shown generally at 30 and includes a receiver means 32, a connector means 36 and a locking means 44. These members cooperate to selectively interconnect plunger 22 to plunger rod 28 to permit only a single use of the syringe.

As disclosed in FIGS. 1-3, receiver 32 is a single piece that can be snapped into an opening 21 in plunger 22. In this embodiment, receiver 32 has a base that includes a neck portion 23 which ends in a head portion 25. Opening 21 has a lip 27 at its entrance that snaps behind head portion 25 when head 25 is inserted to retain receiver 32. A second embodiment is show in FIG. 5 wherein receiver 32 is integrally formed with and extends from plunger 22 on the side opposite the needle. As should be appreciated by one of ordinary skill there are numerous ways in which receiver 32 could be affixed to plunger 22.

In the preferred embodiment, receiver 32 is designed with fingers 35 that are normally biased outwardly in the direction of the inner walls of housing 14, this can be seen in FIG. 3. It should be understood that the fingers could engage the inner walls, but they only need to expand to prevent locking sleeve 44 from sliding back over them once they have been released. The fingers 35 can be biased inwardly to capture connector 36 and can be held in place by the locking sleeve 44 as illustrated in FIG. 2. Preferably, the inner wall of each finger is inwardly tapered at 37 to facilitate insertion of connector 36 during assembly, and has a lip 39 at the end of the taper to capture the connector 36 during use. As will be described more fully below, the retention of connector 36 is obtained through the sliding of locking sleeve 44 over receiver 32 to prevent the fingers of receiver 32 from expanding outwardly to release connector 36.

Connector 36 is formed at the end of plunger rod 28, adjacent receiver 32. In the disclosed embodiment, connector 36 is formed by reducing the outer diameter of plunger rod 28 at 38. The outer diameter of plunger rod 28 is reduced substantially to form a neck portion 40 which ends in a head portion 42. Preferably, the outside diameter of head portion 42 is slightly larger than the inside diameter of receiver 32 at the lip portions 39 so that the head portion 42 is captured behind the lip portions when the fingers 35 are biased inwardly. Sleeve 44 is free to slide over receiver 32 when fingers 35 are biased inwardly to entrap head 42 within receiver 32. When locking sleeve 44 is positioned about receiver 32, head 42 is prevented from escaping so that the plunger rod 28 can pull plunger 22 rearwardly to create a vacuum within chamber 20 and draw fluid into chamber 40.

With reference to FIGS. 4 and 6, the preferred embodiment of the locking sleeve 44 will now be described. As illustrated, locking sleeve 44 is a tubular sleeve having a longitudinal opening 49. Opening 49 allows the sleeve to be easily inserted into housing 14, and to expand to engage the inner wall 26 once it is inserted. To insert sleeve 44, the tube is squeezed to close opening 49 which reduces its outside diameter allowing it to be easily inserted into housing 14. Once sleeve 44 is inserted, it expands to engage the inner wall 26.

With reference to FIG. 5, a further embodiment of the locking sleeve 44 is illustrated. In this embodiment, the locking sleeve has been modified so that the split side wall is not necessary and to provide less surface contact between the inner wall of locking sleeve 44 and fingers 35. The wall of the locking sleeve is configured so that it normally biases outwardly. This is accomplished by providing a living hinge type connection at 51. As illustrated, hinge 51 is recessed slightly into the inner wall of sleeve 44 to bias the sides of sleeve 44 outwardly. To insert sleeve 44 of this embodiment, the walls are squeezed inwardly against the bias of hinge 51. Once inserted, the walls spring back against the inner wall 25 of housing 14. To facilitate the release of fingers 35, the inner wall of sleeve 44 is tapered to reduce the surface contact between the inner wall and the fingers.

To facilitate the drawing of the coupling means 30 away from needle 16, the opposed ends of locking sleeve 44 have different configurations. On the front face 46 of locking sleeve 44, the edge 48, where the face 46 intersects the outer walls 47 of locking sleeve 44, forms a sharp edge. Preferably, the outside diameter of locking sleeve 44 at edge 48 is substantially equal to the inside diameter of outer housing 14. In this way, the corners drag upon the inner walls of housing 14 as the collar is pulled rearwardly. This dragging causes the plunger 22 to abut the front face 46 of the locking sleeve 44 preventing connector 36 from being released from receiver 32 as the plunger rod 22 is being drawn away from needle 16. This can be seen in FIG. 2. The back face 50 of locking sleeve 44 has an edge 52 which is slightly tapered. The tapered edge 52 permits plunger 22 to be easily drawn away from needle 16.

After plunger rod 28 has been drawn rearwardly to draw sufficient fluid into chamber 20 as shown in FIG. 2, it is then, as in conventional syringes, pushed in the direction of the needle to issue fluid from needle 16, as shown in FIG. 3. As plunger rod 28 is forced toward needle 16, the edges 48 of locking sleeve 44 engage the inner wall of housing 14 causing locking sleeve 44 to stop while receiver 32 continues. As the travel of rod 22 continues, locking sleeve 44 releases receiver 32 freeing fingers 35 and allowing fingers 35 to spring outwardly against or at least in the direction of the inner walls 26 of housing 14. As the travel of plunger rod 28 continues, rod 28 at point 38 engages the back face 50 of sleeve 44 and pushes it along against the frictional engagement of edge 48 with the interior wall of housing 14. This forces sleeve 44 to a low position within the housing as illustrated in FIG. 3. In this low position, locking sleeve 44 is wedged in place within the interior of housing 14 a spaced distance from receiver 32 to prevent it from being moved in the direction of plunger 22. Additionally, even if the locking sleeve 44 could be moved in the direction of receiver 32, the fingers 35, being spread open, would prevent the locking sleeve from being positioned over the receiver without breaking the housing 14. Thus, the syringe is limited to one use.

With the locking sleeve 44 in the position shown in FIG. 3, plunger 22 cannot be pulled by rod 28 in a direction opposite needle 16 after the initial use, because there is nothing to retain connector 36 in receiver 32. Therefore, if rod 28 is drawn rearwardly, it will be released from syringe 10 rendering the syringe useless.

To assemble the unit, the plunger 22 and receiver 32 are assembled and the locking sleeve 44 is mounted over receiver 32 and inserted into housing 14. The plunger is forced to is forced to its lowest position in the housing during assembly of the syringe. This can be done by using a tool to push the assembly to the base of the syringe. As should be appreciated, other methods of assembly are available to those of ordinary skill in the art. After the plunger 22 and receiver 32 are in place, the plunger rod 28 can be inserted and forced into receiver 32. To facilitate insertion of rod 28, head portion 42 has a longitudinal slot 60 which allows the diameter of head portion 42 to be reduced slightly when it is inserted. Once inserted, the head portion expands to its original diameter. This can be seen in FIG. 5. With reference to FIG. 1, the assemble syringe is illustrated. At this point, the plunger rod 28 is locked in position and the unit is ready to be used as an ordinary syringe for one use.

It will be apparent to those skilled in the art that the foregoing disclosure is exemplary in nature rather than limiting, with the invention being limited only by the appended claims:

What is claimed is:
1. A self destructing syringe comprising:
an outer housing having an interior cavity;
a hollow needle affixed to the end of said outer housing, said needle having a passage in communication with the interior cavity of said housing such that fluid can be drawn into said cavity through said passage in said needle;
a plunger operatively received within said housing and adapted to reciprocate within said interior cavity;
a plunger rod received within said housing and adapted to reciprocate within said interior cavity, said plunger rod being selectively coupled to said plunger to control the movement of said plunger within said housing when coupled to said plunger;
a coupling means for selectively coupling said plunger and said plunger rod such that said plunger and plunger rod are initially coupled to permit said plunger to be drawn away from said needle by said plunger rod to draw fluid into said cavity and to be pushed toward said needle to issue fluid from said cavity and said needle; said coupling means automatically disconnecting said plunger and said plunger rod after said plunger has been drawn away from said needle;
said coupling means including;
a connector means for selectively interconnecting said plunger rod and said plunger, said connector means extending outwardly from said rod in the direction of said plunger;
a receiver means for selectively joining the plunger rod and the plunger, said receiver means having a head member at one end for insertion into said plunger to secure said receiver to said plunger and expandable fingers at the opposite end adapted to receive and capture said connector means, said receiver means being generally tubular with the walls of said tube being split longitudinally such that said receiver means is free to expand for receipt of said connector means;
a locking means operatively mounted upon said plunger rod for engaging said receiver means and locking said connector means within said receiver means during the initial drawing of said plunger away from said needle and for automatically releasing said receiver means after said initial drawing of said plunger;
whereby said plunger cannot be drawn away from said needle more than once.

2. The self destructing syringe of claim 2, wherein said connector means has a shaft projecting from said plunger rod, said shaft ending in an enlarged portion adapted to be received by said receiver means.

3. The self destructing syringe of claim 1, wherein said receiver means has at least two fingers which are normally biased outwardly into engagement with the inner wall of the housing; said fingers being adapted to be biased inwardly to capture said connector means and to be locked in said inwardly biased position by said locking means when said plunger rod and plunger are connected; said fingers springing outwardly against the inner wall of said housing when said locking means is removed;
whereby said plunger rod is disconnected from said plunger and said plunger is immobile with said fingers opened.

4. The self destructing needle of claim 1, wherein said housing and said needle form an integral sealed unit.

5. A self destructing syringe comprising:
an outer housing having an interior cavity;
a hollow needle affixed to the end of said outer housing, said needle having a passage in communication with the interior cavity of said housing such that fluid can be drawn into said cavity through said passage in said needle;
a plunger operatively received within said housing and adapted to reciprocate within said interior cavity;
a plunger rod received within said housing and adapted to reciprocate within said interior cavity, said plunger rod being selectively coupled to said plunger to control the movement of said plunger within said housing when coupled to said plunger;
a coupling means for selectively coupling said plunger and said plunger rod such that said plunger and plunger rod are initially coupled to permit said plunger to be drawn away from said needle by said plunger rod to draw fluid into said cavity and to be pushed toward said needle to issue fluid from said cavity and said needle; said coupling means automatically disconnecting said plunger and said plunger rod after said plunger has been drawn away from said needle;

said coupling means including:
a connector means extending outwardly from said plunger rod in the direction of said plunger;
a receiver means for selectively joining the plunger rod and the plunger, said receiver means having a head member at one end for insertion into said plunger to secure said receiver to said plunger and expandable fingers at the opposite end adapted to receive and capture said connector means, said receiver means being generally tubular with the walls of said tube being split longitudinally such that said receiver means is free to expand for receipt of said connector means, said connector means having a shaft projecting from said plunger rod, said shaft ending in an enlarged portion adapted to be received by said receiver means;
a locking means operatively mounted upon said plunger rod for engaging said receiver means and locking said plunger rod within said receiver means during the initial drawing of said plunger away from said needle and for automatically releasing said receiver means after said initial drawing of said plunger, said locking means including a tubular sleeve having an inside diameter greater than the outside diameter of said receiver means such that said locking means can slide over said receiver means preventing said receiver means from expanding; and
whereby said plunger cannot be drawn away from said needle more than once.

6. A self destructing syringe comprising:
an outer housing having an interior cavity;
a hollow needle affixed to the end of said outer housing, said needle having a passage in communication with the interior cavity of said housing such that fluid can be drawn into said cavity through said passage in said needle;
a plunger operatively received within said housing and adapted to reciprocate within said interior cavity;
a plunger rod received within said housing and adapted to reciprocate within said interior cavity, said plunger rod being selectively coupled to said plunger to control the movement of said plunger within said housing when coupled to said plunger;
a coupling means for selectively coupling said plunger and said plunger rod such that said plunger and plunger rod are initially coupled to permit said plunger to be drawn away from said needle by said plunger rod to draw fluid into said cavity and to be pushed toward said needle to issue fluid from said cavity and said needle; said coupling means automatically disconnecting said plunger and said plunger rod after said plunger has been drawn away from said needle;
said coupling means including;
a connector means extending outwardly from said plunger rod in the direction of said plunger;
a receiver means for selectively joining the plunger rod and the plunger, said receiver means having a head member at one end for insertion into said plunger to secure said receiver to said plunger and expandable fingers at the opposite end adapted to receive and capture said connector means;
a locking means operatively mounted upon said plunger rod for engaging said receiver means and locking said plunger rod within said receiver means during the initial drawing of said plunger away from said needle and for automatically releasing said receiver means after said initial drawing of said plunger, said locking means including a tubular sleeve having an inside diameter greater than the outside diameter of said receiver means such that said locking means can slide over said receiver means preventing said receiver means from expanding, said locking means having an outside diameter substantially equal to the inside diameter of said hollow outer housing, and opposed ends with the end closest said receiver being at substantially a right angle to the outer wall of said locking means and the end farthest from said receiver being slightly tapered at the juncture of said end with the outer wall of said locking means such that said locking means is forced about said receptacle as said plunger is drawn away from said needle and is held within said hollow outer housing as said plunger is pushed in the direction of said needle such that said locking means is disengaged from said receiver;
whereby said receptacle is free to expand and release said connector upon further attempts to draw said plunger away from said needle.

7. A self destructing syringe comprising:
an outer housing having an interior cavity;
a hollow needle affixed to the end of said outer housing, said needle having a passage in communication with the interior cavity of said housing such that fluid can be drawn into said cavity through said passage in said needle;
a plunger operatively received within said housing and adapted to reciprocate within said interior cavity;
a plunger rod received within said housing and adapted to reciprocate within said interior cavity, said plunger rod being selectively coupled to said plunger to control the movement of said plunger within said housing when coupled to said plunger;
a coupling means for selectively coupling said plunger and said plunger rod such that said plunger and plunger rod are initially coupled to permit said plunger to be drawn away from said needle by said plunger rod to draw fluid into said cavity and to be pushed toward said needle to issue fluid from said cavity and said needle; said coupling means automatically disconnecting said plunger and said plunger rod after said plunger has been drawn away from said needle;
said coupling means including separable mating members including a receiver member and a connector member, said receiver member being adapted to accept said connector member, one of said members being affixed to said plunger and the other member of said members being affixed to said plunger rod;
said connector member extending outwardly from said plunger rod in the direction of said plunger;
said receiver member selectively joining the plunger rod and the plunger, said receiver member having a head portion at one end for insertion into said plunger to secure said receiver member to said plunger and expandable fingers at the opposite end adapted to receive and capture said connector member;
a locking member adapted to selectively interlock said mating members when they are interconnected, said locking member operatively mounted upon said plunger rod for engaging said receiver member and locking said plunger rod within said receiver member during the initial drawing of said plunger away from said needle and for automatically releasing said receiver member after said initial drawing of said plunger, said locking member including a tubular sleeve reciprocally mounted upon said plunger rod adjacent said connector member, said sleeve being adapted to slide over said receiver member upon initial coupling of said receiver and said connector to interlock said receiver and said connector member, and to slide away from said connector, to free said connector after said plunger has been drawn a first time such that said receiver and said connector are unlocked and free to disconnect if said plunger rod is pulled a second time;

whereby said plunger cannot be drawn away from said needle more than once.

8. The self destructing needle of claim 7, wherein said receiver has outwardly biased fingers which spring outwardly upon said sleeve sliding away from said connector, whereby said sleeve cannot be repositioned about said receiver.

9. An automatically releasing coupler for use with a syringe to limit the syringe to a single use, said syringe having a tubular body, a needle attached to one end of said body, a plunger rod inserted into the opposite end of said body and a plunger reciprocally received within said body between said plunger rod and said plunger; said coupler comprising:

a receiver means for selectively joining the plunger rod and the plunger, said receiver means having a head member at one end for insertion into said plunger to secure said receiver to said plunger and expandable fingers at the opposite end adapted to receive and capture said plunger rod;

a locking means operatively mounted upon said plunger rod for engaging said receiver means and locking said plunger rod within said receiver means during the initial drawing of said plunger away from said needle and for automatically releasing said receiver means after said initial drawing of said plunger;

said locking means having an outside diameter substantially equal to the inside diameter of said hollow outer housing, said locking means having opposed ends with the end closest said receiver being at substantially a right angle to the outer wall of said locking means and the end farthest from said receiver being slightly tapered at the juncture of said end with the outer wall of said locking means such that said locking means is forced about said receptacle as said plunger is drawn away from said needle and is held within said hollow outer housing as said plunger is pushed in the direction of said needle such that said locking means is disengaged from said receiver;

whereby said plunger rod disengages from said receiver means upon any further efforts to pull said plunger away from said needle.

10. The self destructing syringe of claim 9, wherein said receiver means has at least two fingers which are normally biased outwardly into engagement with the inner wall of the housing; said fingers being adapted to be biased inwardly to capture said connector means and to be locked in said inwardly biased position by said locking means when said plunger rod and plunger are connected; said fingers springing outwardly against the inner wall of said housing when said locking means is removed;

whereby said plunger rod is disconnected from said plunger and said plunger is immobile with said fingers opened.

11. A self destructing syringe comprising:

a hollow syringe body with a needle affixed thereto;

a plunger reciprocally mounted within said body;

a rod received within said body for selectively controlling said plunger;

a coupling means for selectively coupling said plunger and said plunger rod and for automatically releasing said plunger and said plunger rod during the reciprocal movement of said plunger;

said coupling means including;

a connector means extending outwardly from said plunger rod in the direction of said plunger;

a receiver means for selectively joining the plunger rod and the plunger, said receiver means having a head member at one end for insertion into said plunger to secure said receiver to said plunger and expandable fingers at the opposite end adapted to receive and capture said connector means;

a locking means operatively mounted upon said plunger rod for engaging said receiver means and locking said plunger rod within said receiver means during the initial drawing of said plunger away from said needle and for automatically releasing said receiver means after said initial drawing of said plunger;

said locking means including a tubular sleeve reciprocally mounted upon said plunger rod adjacent said connector means, said sleeve being adapted to slide over said receiver means upon initial coupling of said receiver and said connector to interlock said receiver and said connector means, and to slide away from said connector, to free said connector after said plunger has been drawn a first time such that said receiver and said connector are unlocked and free to disconnect if said plunger rod is pulled a second time.

12. The self destructing syringe of claim 11, wherein said receiver means has at least two fingers which are normally biased outwardly into engagement with the inner wall of the housing; said fingers being adapted to be biased inwardly to capture said connector means and to be locked in said inwardly biased position by said locking means when said plunger rod and plunger are connected; said fingers springing outwardly against the inner wall of said housing when said locking means is removed;

whereby said plunger rod is disconnected from said plunger and said plunger is immobile with said fingers opened.

13. The self destructing needle of claim 12, wherein said receiver has outwardly biased fingers which spring outwardly upon said sleeve sliding away from said connector, whereby said sleeve cannot be repositioned about said receiver.

14. The self destructing syringe of claim 11, wherein said receiver means is generally tubular with the walls of said tube being split longitudinally to form at least two outwardly biased fingers.

15. The self destructing syringe of claim 11, wherein said connector means has a shaft projecting from said plunger rod, said shaft ending in an enlarged portion adapted to be received by said receiver means.

16. The self destructing syringe of claim 11, wherein said locking means includes a tubular sleeve having an inside diameter greater than the outside diameter of said receiver means such that said locking means can slide over said receiver means preventing said receiver means from expanding.

17. The self destructing syringe of claim 11, wherein said receiver means is generally tubular with the walls of said tube being split longitudinally such that said receiver means is free to expand for receipt of said connector means;

said connector means has a shaft projecting from said plunger rod, said shaft ending in an enlarged portion adapted to be received by said receiver means; and said locking means includes a tubular sleeve having an inside diameter greater than the outside diameter of said receiver means such that said locking means can slide over said receiver means preventing said receiver means from expanding.

18. The self destructing syringe of claim 11, wherein said locking means has an outside diameter substantially equal to the inside diameter of said hollow outer housing, said locking means having opposed ends with the end closest said receiver being at substantially a right angle to the outer wall of said locking means and the end farthest from said receiver being slightly tapered at the juncture of said end with the outer wall of said locking means such that said locking means is forced about said receptacle as said plunger is drawn away from said needle and is held within said hollow outer housing as said plunger is pushed in the direction if said needle such that said locking means is disengaged from said receiver;

whereby said receptacle is free to expand and release said connector upon further attempts to draw said plunger away from said needle.

* * * * *

UNITED STATES PATENT AND TRADEMARK OFFICE
CERTIFICATE OF CORRECTION

PATENT NO. : 5,149,323

DATED : September 22, 1992

INVENTOR(S) : John P. Colonna

It is certified that error appears in the above-indentified patent and that said Letters Patent is hereby corrected as shown below:

On the title page, item [54] and column 1, line 2, delete "DOUBLE".

Signed and Sealed this

Fifteenth Day of November, 1994

Attest:

BRUCE LEHMAN

*Attesting Officer*     *Commissioner of Patents and Trademarks*